United States Patent [19]

Calcagno

[11] 4,298,524
[45] Nov. 3, 1981

[54] PREPARATION OF THION- AND THIOL-CARBAMIC ESTERS

[75] Inventor: Giancarlo Calcagno, Milan, Italy

[73] Assignee: Ligurchim S.r.l., Genoa, Italy

[21] Appl. No.: 111,109

[22] Filed: Jan. 10, 1980

[30] Foreign Application Priority Data

Aug. 6, 1979 [IT] Italy ............................. 24940 A/79

[51] Int. Cl.³ .................. C07C 155/02; C07D 211/06
[52] U.S. Cl. ........................... 260/239 BF; 260/455 A
[58] Field of Search ...................... 260/455 A, 239 BF

[56] References Cited

U.S. PATENT DOCUMENTS 2,691,635 10/1954 Harris et al. ..................... 260/455 A Primary Examiner—Henry R. Jiles
Assistant Examiner—Robert C. Whittenbaugh
Attorney, Agent, or Firm—Stevens, Davis, Miller & Mosher

[57] ABSTRACT

Thion-carbamic esters are obtained reacting in a single stage an alkaline xanthogenate, an amine and an oxidizer, according to the reaction:

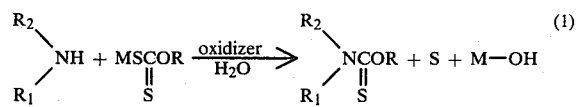

wherein:

R, $R_1$, $R_2$ each are an alkyl, alkylaromatic, olefinic, cycloolefinic, cycloparaffinic, acetylenic, heterocyclic radical, and may further contain many other different chemical functions, and $R_1$ may also be H; and

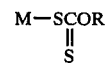

is a xanthogenate, wherein M is a metal, preferably alkaline.

15 Claims, No Drawings

PREPARATION OF THION- AND THIOL-CARBAMIC ESTERS

BACKGROUND OF THE INVENTION

The importance of some thiol-carbamic esters, in the agricultural field, is well known to the skilled in the art, and equally known are the technological difficulties which arise in their preparation. The methods and processes adopted at present require in fact the use of very unpleasant reagents, being poisonous, bad smelling, expensive and causing pollution, such as phosgene, carbonyl sulphide, ethyl mercaptan, metallic sodium, ethyl chlorothiolformate, and require the use of installations which are always complex, costly and generally undesired for ecological purposes.

It is thus easy to understand why searches are being carried out with such interest and intenseness, for the purpose of saving the production of thiolcarbamates from such a precarious situation.

In the sphere of such searches, the present invention provides a fully satisfactory solution of the problem, starting from the consideration that the thiol-carbamic esters can be obtained by isomerization of corresponding thion-carbamic esters, and providing for original and particularly simple and efficient methods both for obtaining the thioncarbamates and for their isomerization into thiolcarbamates.

SUMMARY OF THE INVENTION

According to a first aspect of the present invention, a method for obtaining thion-carbamic esters consists in reacting, in a single stage, an alkaline xanthogenate, an amine and an oxidizer, according to the reaction:

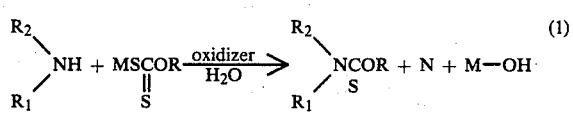

wherein:
R, $R_1$, $R_2$ each are an alkyl, alkylaromatic, olefinic, cycloolefinic, cycloparaffinic, acetylenic, heterocyclic radical. Moreover, such radicals may contain many other different chemical functions and $R_1$ may also be H; and

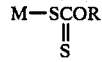

is a xanthogenate wherein M is metal, preferably alkaline.

In the reaction (1) as oxidizers can be used chlorine, iodine, copper sulphate, tetrathionate, chloramine T, persulphate, oxygen, atmospheric oxygen in the presence of catalysts, and furthermore, hydrogen peroxide and hypochlorites. It is interesting to observe how, according to analytical literature, hydrogen peroxide is used for proportioning alkaline xanthogenates, on account of its quantitatively destructive action; hence, at first sight, it would not seem suitable for the purpose intended by the reaction (1). Vice-versa, it has been found that, by using hydrogen peroxide in this reaction, the reaction products—evidently due to the presence of amine—are not decomposition products: quite unexpectedly and in a fully particular way, the thion-carbamic esters are obtained.

The reaction (1) is preferably carried out in water, even if alcohols and other solvents are by all means acceptable. The reaction temperature (the reaction is exothermic) is to be kept between approx. 0° C. and approx. 50° C. and over, preferably between 10° and 30° C.

The reaction times do not exceed a few hours, but normally, for the thioncarbamates which are of actual interest at present, such times are reduced to a few minutes, practically to the times for elimination of the heats of reaction. The pH of reaction are and have to be definitely alkaline.

According to a further aspect of the present invention, the thion-carbamic esters may be obtained, by a chemical process similar to that of the reaction (1), starting from dixanthogenate instead of xanthogenate and, precisely, by reacting in a single stage a dixanthogenate and a non-tertiary amine, according to the reaction:

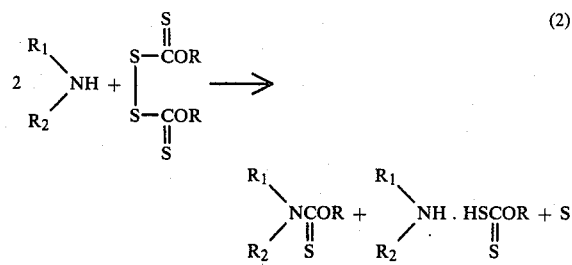

said reaction actually taking place also when the reaction (1) is carried out, as soon as the xanthogenate and the oxidizer have reacted between them to produce dixanthogenate. The reaction (2) tends to explain the mechanism of the reaction (1) to which it leads back by simply operating the addition of an alkali and an oxidizer.

According to an even further aspect of the present invention, the thiol-carbamate isomers of the thion-carbamic esters obtained with either of the reactions (1) and (2) (but preferably with the first reaction) are very profitably obtained by carrying out the reaction of isomerization:

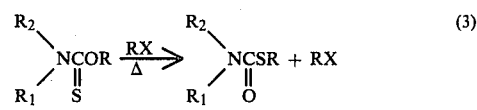

wherein RX is an ethyl halide; and $R_1$, $R_2$, R are the radicals already specified above for the previous reactions;
at temperatures between 120° and 200° C., preferably about 150° C., to accelerate the reaction.

It is important to note how the fact of producing thiolcarbamates through the production of thioncarbamates, by means of the aforespecified reactions (1), (2) and (3), provides very important advantages, among which it will be appropriate to place in particular evidence:

the versatility: it is possible to pass from one carbamate to another (and hence, from one thiolcarbamate to another) by appropriately choosing the radicals R, $R_1$, $R_2$;

the easy use of the reagents which include, as has been seen, the alkaline xanthogenates, the hypochlorites and various aqueous means;

the easiness in finding the reagents (the xanthogenates are found on the market as flotation agents) and, in any case, their very easy preparation;

the ecological properties: no bad smells, waters being already intrinsically treated with oxidizers and having no organic substances.

the simplicity of the technological structures: no complicated equipment, nor gas-tight equipment for poison gases (such gases being inexistent);

the high yields, which result from the following examples.

The invention will now be described in a more clear and practical way through some examples, which however do not form any limitation whatsoever of the contents of the invention itself.

EXAMPLE 1: Production of ethyl N,N-hexamethylenethioncarbamate 50 gr of hexamethyleneimine are added to 250 cc of an aqueous solution containing 95 gr of potassium ethylxanthogenate. The pH is about 12.

A solution of 400–450 cc of sodium hypochlorite with 9% active chlorine is then slowly added by stirring, in about 30', keeping the temperature below 30° C. There is the almost immediate formation of ester and sulphur which are separated by the aqueous solution.

The thion-carbamate is obtained with an almost quantitative yield.

The reaction can be conducted continuously, in a cooled reaction vessel, by proportionally feeding and discharging the reagents and, respectively, the products obtained.

EXAMPLE 2: Production of ethyl N,N-disobutylthioncarbamate

One operates exactly as in Example 1, but using an amine the diisobutylamine in the amount of 65 gr.

The pH must be kept at about 12, with small additions of NaOH. The yield of thion-carbamate ester is higher than 90%.

EXAMPLE 3: Production of ethyl N,N di-n-propylthioncarbamate

One proceeds as in Example 1, but using as amine the di-n-propylamine in the quantity of 51 gr. The yield of ester is beyond 90%.

EXAMPLE 4: Production of ethyl N,N-hexamethylenethioncarbamate 170 gr. of potassium ethylxanthogenate and 116 cc of hexamethyleneimine are dissolved in 500 cc of $H_2O$.

180 cc of $H_2O_2$ at 34%, diluted with 300 cc of $H_2O$, are added drop by drop to this solution by stirring, at a temperature below 35° C. and with a pH of about 12. The ester being formed is separated from the sulphur and from the aqueous solution, washed and distilled. 160 gr are obtained, equal to about 85% of the yield. Also this reaction can be carried out continuously.

EXAMPLE 5: Production of ethyl N,N-hexamethylenethioncarbamate

In an aqueous means, 1 mole of ethyl dixanthogenate is reacted with 2 moles of hexamethyleneimine. This allows to obtain, almost quantitatively, 1 mole of N,N-hexamethylenethioncarbamate, 1 mole of ethylxanthogenate of hexamethyleneimine and 1 gram-atom of sulphur. The reaction is exothermic and has to be kept below 30° C.

EXAMPLE 6: Production of ethyl N,N-hexamethylenethiolcarbamate

To 100 gr of N,N-hexamethylene thion-carbamic ester, obtained according to one of the previous Examples 1, 4 or 5, there are added 10 gr of ethyl iodide as catalyst. Heating is effected at 150° C. in a closed tube for 30'-1 hour. Isomerization is total (gas chromatography and I.R.) and the recovery after distillation is over 95%, giving an ethyl N,N-hexamethylenethiolcarbamate at 98.5–99%. The catalyst is recovered.

The process carried out continuously gives the same results.

EXAMPLE 7: Production of ethyl N,N-di-n-propylthiolcarbamate

To 100 gr of ethyl N,N-di-n-propylthioncarbamate, obtained according to the previous Example 3, there are added 10 gr of ethyl bromide as catalyst. Heating is effected at 150° C. in a closed tube for 3 hours. Distillation is carried out and 96 gr of ethyl N,N-di-n-propylthiolcarbamate at 98% are obtained. The catalyst is recovered.

EXAMPLE 8: Production of ethyl N,N-hexamethylenetiolcarbamate 100 gr of N,N-hexamethylenethioncarbamate, obtained according to anyone of the previous examples 1, 4 or 5, are treated with 100 cc of ethanol and 5 gr of ethyl iodide as catalyst. Heating is effected at 150° C. in a closed tube for 3 hours. Distillation is carried out and 97 gr of thiolester at 98.5% are obtained. The catalyst is recovered.

EXAMPLE 9: Production of ethyl N,N-diisobutylthiolcarbamate

One operates exactly as in Example 6, but starting from N,N-diisobutylthioncarbamate. Isomerization is complete. The recovery and the concentration of the thiolester are higher than 97%. The catalyst, ethyl iodide, is recovered.

EXAMPLE 10: Production of:

ethyl N,N-hexamethylenethiolcarbamate ethyl N,N-di-n-propylthiolcarbamate ethyl N,N-di-isobutylthiolcarbamate One operates as in Example 6, but with ethyl iodide percentages varying between 2 to 5% in weight, at temperatures of about 150° C., and for lengths of time varying between 3 to 5 hours.

The same results are obtained. The catalyst is recovered.

I claim:

1. Method for obtaining thion-carbamic esters, consisting in reacting in a single stage an alkaline xanthogenate, an amine and an oxidizer, according to the reaction:

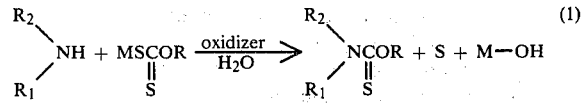

wherein:

R is a lower alkyl; $R_1, R_2$ are lower alkyls, cycloparaffinic radicals or $R_1$ and $R_2$ together with the nitrogen to which they are attached form a heterocyclic ring;

and

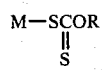

is a xanthogenate, wherein M is a metal.

2. Method as in claim 1, wherein the oxidizer may be chlorine, iodine, copper sulphate, tetrathionate, chloramine T, persulphate, hydrogen peroxide, hypochlorite.

3. Method as in claim 1, wherein the reaction temperature varies between 0° and 50° C. and over.

4. Method as in claim 3, wherein the reaction temperature varies between 10° and 30° C.

5. Method as in claim 1, wherein the reaction times vary between a few minutes and a few hours, and the pH of reaction is definitely alkaline.

6. Method as in claim 1, carried out discontinuously.

7. Method as in claim 1, carried out continuously.

8. Method for obtaining thion-carbamic esters, consisting in reacting in a single stage a dixanthogenate and a non-tertiary amine, according to the reaction:

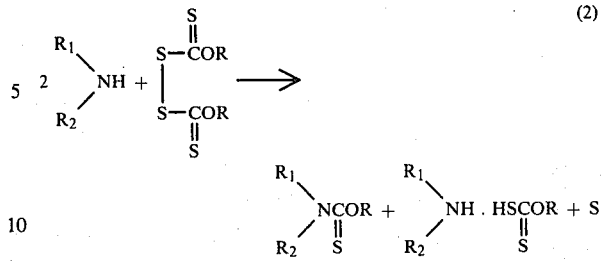

wherein:

R is a lower alkyl; $R_1, R_2$ are lower alkyls, cycloparaffinic radicals or $R_1$ and $R_2$ together with the nitrogen to which they are attached form a heterocyclic ring.

9. Method as in claim 8, carried out discontinuously.

10. Method as in claim 8, carried out continuously.

11. Method for obtaining the thiolcarbamic isomers from the thion-carbamic esters obtained with a method according to claim 1, comprising the reaction of isomerization:

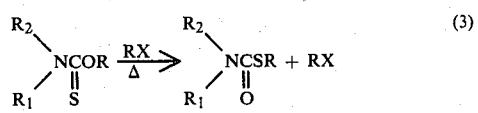

wherein

RX is an ethyl halide, and $R_1$, $R_2$, R are radicals as defined in claim 1.

12. Method as in claim 11, wherein the reaction temperature is of about 150° C.

13. Method as in claim 1, carried out in the presence of inert solvents.

14. Method as in claim 8, carried out in the presence of inert solvents.

15. Method as in claim 12, carried out in the presence of inert solvents.

* * * * *